(12) United States Patent
Enomoto

(10) Patent No.: US 8,885,795 B2
(45) Date of Patent: Nov. 11, 2014

(54) RADIATION DETECTOR, RADIOGRAPHIC IMAGE CAPTURING SYSTEM, RADIATION DETECTION METHOD, AND RADIATION DETECTION PROGRAM STORAGE MEDIUM

(75) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 423 days.

(21) Appl. No.: 13/253,970

(22) Filed: Oct. 6, 2011

(65) Prior Publication Data

US 2012/0091352 A1    Apr. 19, 2012

(30) Foreign Application Priority Data

Oct. 14, 2010   (JP) ................. 2010-231613

(51) Int. Cl.
*A61B 6/00* (2006.01)
*H05G 1/64* (2006.01)
*H04N 5/32* (2006.01)
*G01D 18/00* (2006.01)

(52) U.S. Cl.
CPC ............. *H04N 5/32* (2013.01); *A61B 6/4233* (2013.01); *A61B 6/4208* (2013.01); *H05G 1/64* (2013.01); *G01D 18/002* (2013.01); *G01D 18/004* (2013.01); *G01D 18/006* (2013.01); *G01D 18/008* (2013.01)
USPC ............. 378/98.8; 378/207; 250/370.09; 250/370.15

(58) Field of Classification Search
CPC .......... H05G 1/08; H05G 1/64; G01D 18/00; G01D 18/002; G01D 18/004; G01D 18/006; G01D 18/008; A61B 6/42; A61B 6/4208; A61B 6/4233

USPC ............. 378/19, 91, 98.8, 207; 250/370.09, 250/370.15
See application file for complete search history.

(56) References Cited

U.S. PATENT DOCUMENTS

| | | | | |
|---|---|---|---|---|
| 5,694,448 A | * | 12/1997 | Morcom | 378/98.8 |
| 5,887,049 A | * | 3/1999 | Fossum | 378/98.8 |
| 5,912,942 A | * | 6/1999 | Schick et al. | 378/98.8 |
| 5,970,113 A | * | 10/1999 | Crawford et al. | 378/19 |
| 6,307,915 B1 | * | 10/2001 | Frojdh | 378/98.8 |

(Continued)

FOREIGN PATENT DOCUMENTS

| | | |
|---|---|---|
| JP | 62-43586 | 2/1987 |
| JP | 4-315985 | 11/1992 |

(Continued)

OTHER PUBLICATIONS

Extended European Search Report dated Sep. 13, 2012 issued in corresponding EP application No. 11184952.7.

(Continued)

*Primary Examiner* — Allen C. Ho
(74) *Attorney, Agent, or Firm* — SOLARIS Intellectual Property Group, PLLC

(57) ABSTRACT

A radiation detector includes an image data detecting unit that detects, as radiographic image data, charge information corresponding to applied radiation; a control unit that determines that radiation has been applied if a read value of the detected charge information is equal to or greater than a threshold value and controls the image data detecting unit to acquire radiographic image data corresponding to radiation that has passed through a subject; and a changing unit that changes the threshold value in accordance with temperature data of the image data detecting unit.

3 Claims, 7 Drawing Sheets

(56) References Cited

U.S. PATENT DOCUMENTS

| | | | |
|---|---|---|---|
| 6,380,528 B1* | 4/2002 | Pyyhtia et al. | 250/208.1 |
| 6,404,854 B1* | 6/2002 | Carroll et al. | 378/98.8 |
| 6,497,511 B1* | 12/2002 | Schmitt et al. | 378/207 |
| 6,737,654 B2* | 5/2004 | Ducourant | 250/370.11 |
| 6,775,351 B2* | 8/2004 | Rinaldi et al. | 378/98.8 |
| 7,277,568 B2* | 10/2007 | Spahn | 382/132 |
| 7,355,183 B2* | 4/2008 | Spahn | 250/370.09 |
| 7,382,859 B2* | 6/2008 | Nokita et al. | 378/98.8 |
| 7,399,974 B2* | 7/2008 | Spahn | 250/370.09 |
| 7,421,063 B2* | 9/2008 | Takenaka et al. | 378/116 |
| 7,629,587 B2* | 12/2009 | Yagi et al. | 250/370.15 |
| 7,822,178 B2* | 10/2010 | Enomoto | 378/91 |
| 7,832,928 B2* | 11/2010 | Topfer et al. | 378/207 |
| 8,097,858 B2* | 1/2012 | Iijima | 250/370.09 |
| 8,119,990 B2* | 2/2012 | Zeller | 250/370.09 |
| 8,340,460 B2* | 12/2012 | Deutschmann | 382/275 |
| 8,523,434 B2* | 9/2013 | Tsuji | 378/207 |
| 8,542,796 B2* | 9/2013 | Sato | 378/62 |
| 8,550,709 B2* | 10/2013 | Nishino et al. | 378/207 |
| 8,760,544 B2* | 6/2014 | Tanabe et al. | 348/244 |
| 2004/0109488 A1 | 6/2004 | Glukhovsky | |
| 2004/0228452 A1 | 11/2004 | Rinaldi et al. | |

FOREIGN PATENT DOCUMENTS

| | | |
|---|---|---|
| JP | 2000-356680 | 12/2000 |
| JP | 2003-307569 A | 10/2003 |
| JP | 2005-013272 A | 1/2005 |
| JP | 2008-132216 | 6/2008 |

OTHER PUBLICATIONS

Partial English language translation of the following: Office action dated Oct. 23, 2012 from the Japanese Patent Office in a Japanese patent application corresponding to the instant patent application. This office action translation is submitted now in order to supplement the understanding of patent document JP 2008-132216, JP2000-356680 and JP04-315985 which are cited in the office action and are being disclosed in the instant Information Disclosure Statement.

Office action dated Nov. 19, from the Japanese Patent Office in a Japanese patent application corresponding to the instant patent application with partial English Translation.

Office action dated Dec. 19, from the Chinese Patent Office in a Chinese patent application corresponding to the instant patent application with partial English Translation.

Partial English language translation of the following: Office action dated Feb. 4, 2014 from the Japanese Patent Office in a Japanese patent application corresponding to the instant patent application. This office action translation is submitted now in order to supplement the understanding of patent document JPS62-43586 which is cited in the office action and is being disclosed in the instant Information Disclosure Statement.

Office action dated Jun. 16, 2014, from the European Patent Office in a European patent application corresponding to the instant patent application.

* cited by examiner

RADIATION DETECTOR, RADIOGRAPHIC IMAGE CAPTURING SYSTEM, RADIATION DETECTION METHOD, AND RADIATION DETECTION PROGRAM STORAGE MEDIUM

CROSS-REFERENCE TO RELATED APPLICATION

This application claims priority under 35 USC 119 from Japanese Patent Application No. 2010-231613 filed on Oct. 14, 2010, the disclosure of which is incorporated by reference herein.

BACKGROUND OF THE INVENTION

1. Field of the Invention

The present invention pertains to a radiation detector, a radiographic image capturing system, a radiation detection method, and a radiation detection program storage medium and particularly relates to a radiation detector, a radiographic image capturing system, a radiation detection method, and a radiation detection program storage medium that capture a radiographic image without having to synchronize with a radiation application action of a radiation applicator.

2. Description of the Related Art

Conventionally, radiographic image capturing systems that perform radiographic imaging for the purpose of medical diagnoses have been known. As one such radiographic image capturing system, there is a radiographic image capturing system that is equipped with a radiation applicator that applies radiation, a radiation detector—such as what is known as a cassette—that detects the radiation that has passed through a subject to capture a radiographic image, and a controller that controls the radiation applicator and the radiation detector.

In recent years, there have been radiation detectors using a flat panel detector (FPD) that is capable of converting the detected radiation into electrical signals. Because dark current, which contributes to noise, exists in a two-dimensional solid-state imaging device such as an FPD, the imaging time of the solid-state imaging device cannot be lengthened unreasonably. For this reason, synchronization of the application action, in which the radiation detector transmits signals to and receives signals from the radiation applicator and in which the radiation applicator applies the radiation, and the imaging action, in which the FPD performs imaging (performs detection of the radiation), is performed.

Specifically, with respect to an imaging request signal from the radiation applicator, the FPD performs initialization of the solid-state imaging device and, after the initialization has been completed, transmits an imaging preparation completion signal to the radiation applicator. After the radiation applicator receives the imaging preparation completion signal, the radiation applicator starts the application of the radiation, ends the application of the radiation after a preset application time has elapsed, and transmits an application end signal to the FPD. When the FPD receives the application end signal, the FPD ends a charge storage action by the solid-state imaging device and transitions to an output action in which the FPD outputs image data of the detected radiographic image to the controller.

In such cases as this, since the radiation applicator is hand-operated in order to control the FPD, the interface for an operator becomes complex and it is necessary to configure the radiation applicator and the FPD as a single integrated system. This leads to an increase in the size and an increase in the complexity of the device.

As a radiation detector that addresses such problems, there is a radiation detector in which the radiographic image is detected by the radiation detector without having to connect to the radiation applicator and without having to transmit signals to and receive signals from the radiation applicator (without having to synchronize with the radiation applicator). For example, Japanese Patent Application Laid-Open (JP-A) Nos. 2005-13272 and 2003-307569 disclose technologies in which the timing of the application of the radiation is determined by the FPD.

As a technology for determining the timing of the application of the radiation that is applied from the radiation applicator in order for the radiation detector to capture a radiographic image of a subject, there is a technology of determining it is the application timing in a case in which charge information (QL value) that has been read out from the solid-state imaging device has reached a predetermined threshold value or greater.

However, the characteristics of the solid-state imaging device of the radiation detector may change in response to temperature. Therefore, the QL value may change due to changes in temperature even if the exposure amount of the radiation detector due to the dose of the radiation applied from the radiation applicator does not change. In such cases, the precision with which the radiation detector detects the radiation drops.

SUMMARY

The present invention provides a radiation detector, a radiographic image capturing system, a radiation detection method, and a radiation detection program storage medium that can improve the precision with which radiation is detected in a radiation detector that determines whether or not radiation has been applied.

A first aspect of the present invention is a radiation detector including: an image data detecting unit that detects, as radiographic image data, charge information corresponding to applied radiation; a control unit that determines that radiation has been applied if a read value of the detected charge information is equal to or greater than a threshold value and controls the image data detecting unit to acquire radiographic image data corresponding to radiation that has passed through a subject; and a changing unit that changes the threshold value in accordance with temperature data of the image data detecting unit.

The control unit determines that radiation has been applied in a case in which the read value of the radiographic image data (charge information) detected by the image data detecting unit is equal to or greater than the threshold value, and controls the image detecting unit to detect the radiographic image data corresponding to the radiation that has passed through the subject. The changing unit changes the threshold value in accordance with the data relating to the temperature (temperature data) of the image data detecting unit.

The read value of the radiographic image data (charge information) changes due to, for example, the characteristics of the image data detecting unit changing because of changes in temperature. Therefore, if the threshold value is set as a fixed value regardless of changes in temperature, the precision with which the radiation detector detects the radiation may drop. Therefore, in the present aspect, the changing unit changes the threshold value in accordance with the temperature data of the image data detecting unit. Thereby, the precision with which the radiation is detected can be improved.

In the above-described aspect, the radiation detector may further include a temperature detecting unit that detects the temperature of the image data detecting unit as the temperature data.

In the above-described aspect, the image data detecting unit may detect offset data of the radiographic image data as the temperature data.

In the above-described aspect, the offset data may be a maximum value of an offset value in a predetermined period.

A second aspect of the present invention is a radiographic image capturing system including: a controller that instructs a setting relating to capturing radiographic data; a radiation applicator that applies radiation on the basis of an instruction from the controller; and the radiation detector of the first aspect, which detects radiographic image data corresponding to the radiation that has been applied from the radiation applicator.

A third aspect of the present invention is a radiation detection method including: causing an image data detecting unit to detect charge information corresponding to applied radiation; determining that radiation has been applied if a read value of the detected charge information is equal to or greater than a threshold value and controlling the image data detecting unit to detect radiographic image data corresponding to radiation that has passed through a subject; and changing the threshold value in accordance with temperature data of the image data detecting unit.

A fourth aspect of the present invention is non-transitory storage medium storing a program causing a computer to execute radiation detection processing, the radiation detection processing including: causing an image data detecting unit to detect charge information corresponding to applied radiation; determining that radiation has been applied if a read value of the detected radiographic image data is equal to or greater than a threshold value and controlling the image data detecting unit to detect radiographic image data corresponding to radiation that has passed through a subject; and changing the threshold value in accordance with temperature data of the image data detecting unit.

As described above, according to the above-described aspects, the precision with which radiation is detected can be improved in a radiation detector that determines whether or not radiation has been applied.

BRIEF DESCRIPTION OF THE DRAWINGS

Exemplary embodiments of the present invention will be described in detail based on the following figures, wherein.

DETAILED DESCRIPTION

First Exemplary Embodiment

A first exemplary embodiment will be described below with reference to the drawings. In the first exemplary embodiment, a case will be described in which a threshold value for determining that radiation has been applied from a radiation applicator in order to capture a radiographic image of a subject is changed in accordance with data relating to the temperature (called temperature data below) of a TFT unit that detects image information (data) of a radiographic image.

Figure 1:
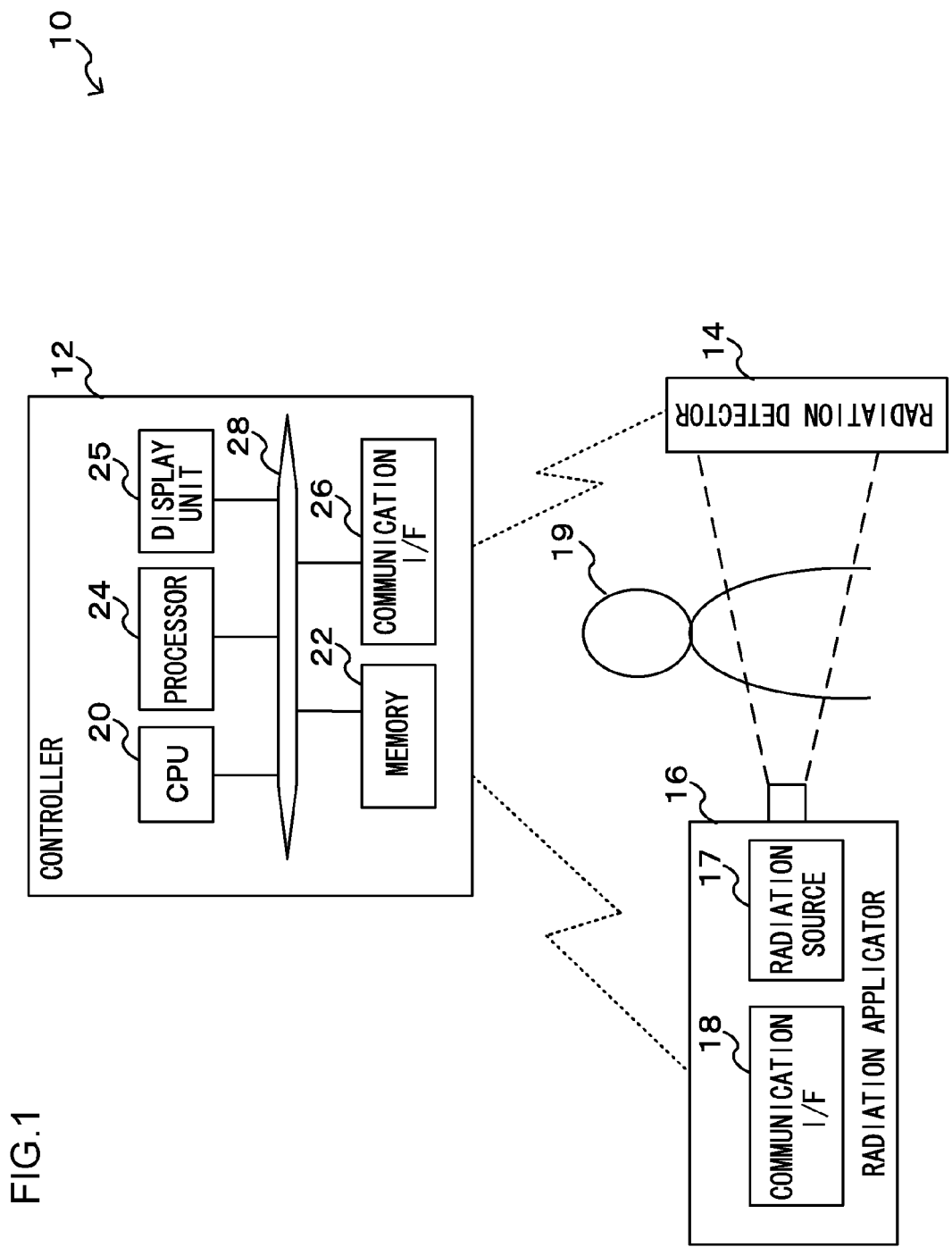
FIG. 1 is a schematic configuration diagram showing an example of the schematic configuration of a radiographic image capturing system pertaining to a first exemplary embodiment.

FIG. 1 shows the schematic configuration of a radiographic image capturing system 10 of the present exemplary embodiment. The radiographic image capturing system 10 is equipped with a radiation applicator 16 that applies radiation (e.g., X-rays) to a subject 19, a radiation detector 14 that detects the radiation that has been applied from the radiation applicator 16 and has passed through the subject 19, and a controller (console) 12 that instructs the capture of a radiographic image, acquires image data from the radiation detector 14, and performs various processings. The radiation that carries image information as a result of being applied from the radiation applicator 16 and passing through the subject 19 positioned in an imaging position is applied to the radiation detector 14.

The controller 12 is wirelessly connected to the radiation detector 14 and executes various controls with respect to the radiation detector 14 by wirelessly transmitting commands and data via a communication interface (I/F) 26. The controller 12 is also wirelessly connected to the radiation applicator 16 and controls the timing when the radiation applicator 16 applies the radiation (e.g., X-rays). The controller 12 is equipped with a central processing unit (CPU) 20, a memory 22, a processor 24, a display unit 25, and the communication I/F 26. The CPU 20, the memory 22, the processor 24, the display unit 25, and the communication I/F 26 are interconnected by a bus 28 such as a CPU bus so as to be capable of sending signals to and receiving signals from each other. The CPU 20 controls the actions of the entire controller 12 by executing various programs that are stored beforehand in the memory 22. The processor 24 acquires the image data from the radiation detector 14 and performs various processings. The display unit 25 displays, for example, the radiographic image received via the communication I/F 26 from the radiation detector 14.

The radiation applicator 16 is equipped with a radiation source 17 and a communication interface (I/F) 18. The radiation applicator 16 is wirelessly connected to the controller 12 via the communication I/F 18 and applies the radiation from the radiation source 17 to the subject 19 at a timing based on the control of the controller 12.

Figure 2:
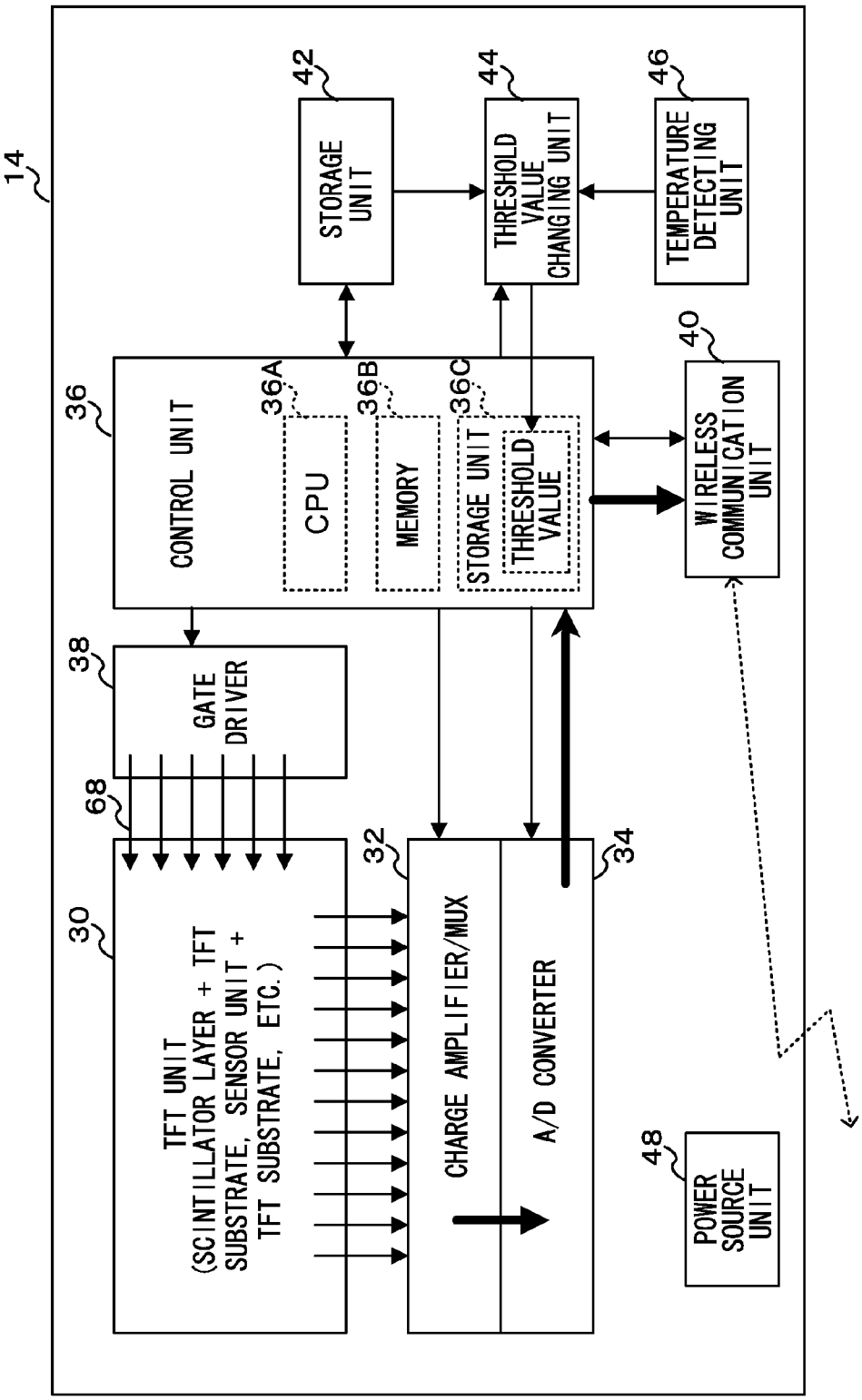
FIG. 2 is a functional block diagram showing an example of the schematic configuration of a radiation detector pertaining to the first exemplary embodiment.

FIG. 2 is a functional block diagram showing an example of the configuration of the radiation detector 14. The radiation detector 14 is a radiation detection panel unit, and examples thereof include flat panel detectors (FPD) and what are known as cassettes.

The radiation detector 14 is equipped with a thin-film transistor (TFT) unit 30, a charge amplifier/multiplexer (MUX) 32, an analog-to-digital (A/D) converter 34, a control unit 36, a gate driver 38, a wireless communication unit 40, a storage unit 42, a threshold value changing unit 44, a temperature detecting unit 46, and a power source unit 48.

Figure 3:
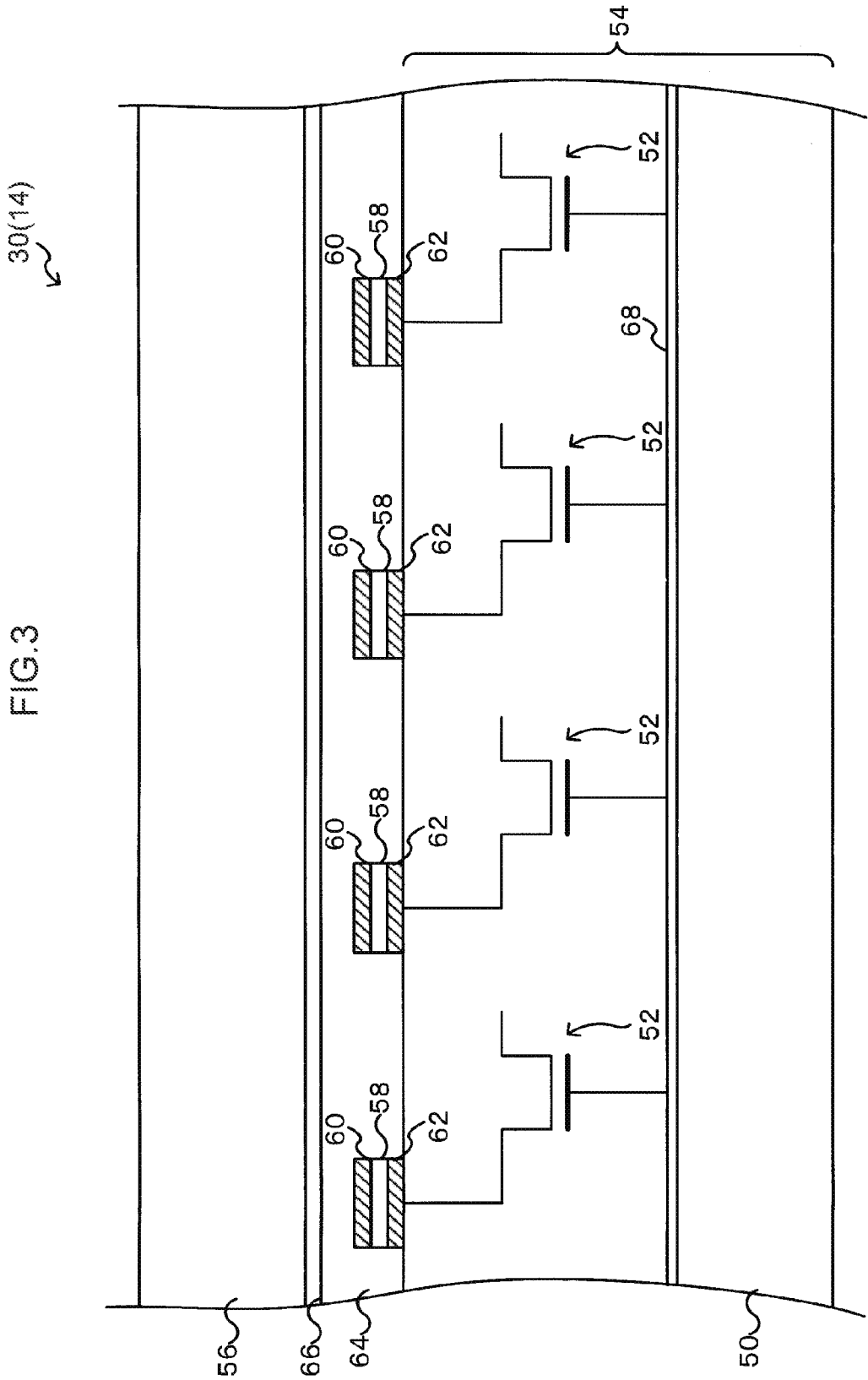
FIG. 3 is a cross-sectional view schematically showing an example of the configuration of a TFT unit of the radiation detector pertaining to the first exemplary embodiment.

The TFT unit 30 detects the applied radiation. FIG. 3 is a cross-sectional view schematically showing an example of the configuration of the TFT unit 30. As shown in FIG. 3, the TFT unit 30 includes a TFT substrate 54 in which switch elements 52 such as TFTs are formed on an insulating substrate 50.

The switch elements 52 are connected to gate lines 68 for switching on and off the switch elements 52. A scintillator layer 56 that converts the radiation made incident thereon into light is formed on the TFT substrate 54. As the scintillator layer 56, for example, a CsI:Tl or GOS ($Gd_2O_2S$:Tb) phosphor or the like can be used. However, the scintillator layer 56 is not limited to these materials.

As the insulating substrate 50, for example, a glass substrate, various types of ceramic substrates, a resin substrate, or the like can be used, but the insulating substrate 50 is not limited to these materials.

Photoconductive layers 58 are placed between the scintillator layer 56 and the TFT substrate 54. The photoconductive layers 58 generates charges when the light into which the radiation has been converted by the scintillator layer 56 is made incident thereon. Bias electrodes 60 for applying a bias voltage to the photoconductive layers 58 are disposed on the surfaces of the photoconductive layers 58 on the scintillator layer 56 side.

Charge collecting electrodes 62 for collecting the charges generated by the photoconductive layers 58 are disposed on the TFT substrate 54. In the TFT substrate 54, the charges collected by the charge collecting electrodes 62 are read out by the switch elements 52.

The charge collecting electrodes 62 are arranged in a matrix (two-dimensionally) on the TFT substrate 54. In correspondence to this, the switch elements 52 are arranged in a matrix on the insulating substrate 50. A planarizing layer 64 for planarizing the top surface of the TFT substrate 54 is formed on the TFT substrate 54. Between the TFT substrate 54 and the scintillator layer 56, an adhesive layer 66 for adhering the scintillator layer 56 to the TFT substrate 54 is formed on the planarizing layer 64.

The radiation may be applied to the radiation detector 14 from the front side on which the scintillator layer 56 is adhered (i.e., the front side is the imaging surface) or may be applied to the radiation detector 14 from the TFT substrate 54 side (back side) (i.e., the back side is the imaging surface). In the case in which the radiation is applied to the radiation detector 14 from the front side, light emission at the upper surface side (the opposite side of the TFT substrate 54 side) of the scintillator layer 56 is relatively strong. In the case in which the radiation is applied to the radiation detector 14 from the back side, the radiation that has passed through the TFT substrate 54 is made incident on the scintillator layer 56, and light emission at the TFT substrate 54 side of the scintillator layer 56 is relatively strong. Charges are generated in the photoconductive layers 58 by the light that has been applied thereto by the scintillator layer 56. Therefore, the sensitivity of the radiation detector 14 with respect to the radiation can be set higher in the case in which the radiation is applied from the front side than in the case in which the radiation is applied from the back side, because the radiation does not pass through the TFT substrate 54 in the case in which the radiation is applied from the front side. In contrast, the resolution of the radiographic image obtained by the imaging is higher in the case in which the radiation is applied from the back side than in the case where the radiation is applied from the front side, because the light emission position of the scintillator layer 56 with respect to the photoconductive layers 58 is closer in the case in which the radiation is applied from the back side.

Figure 4:
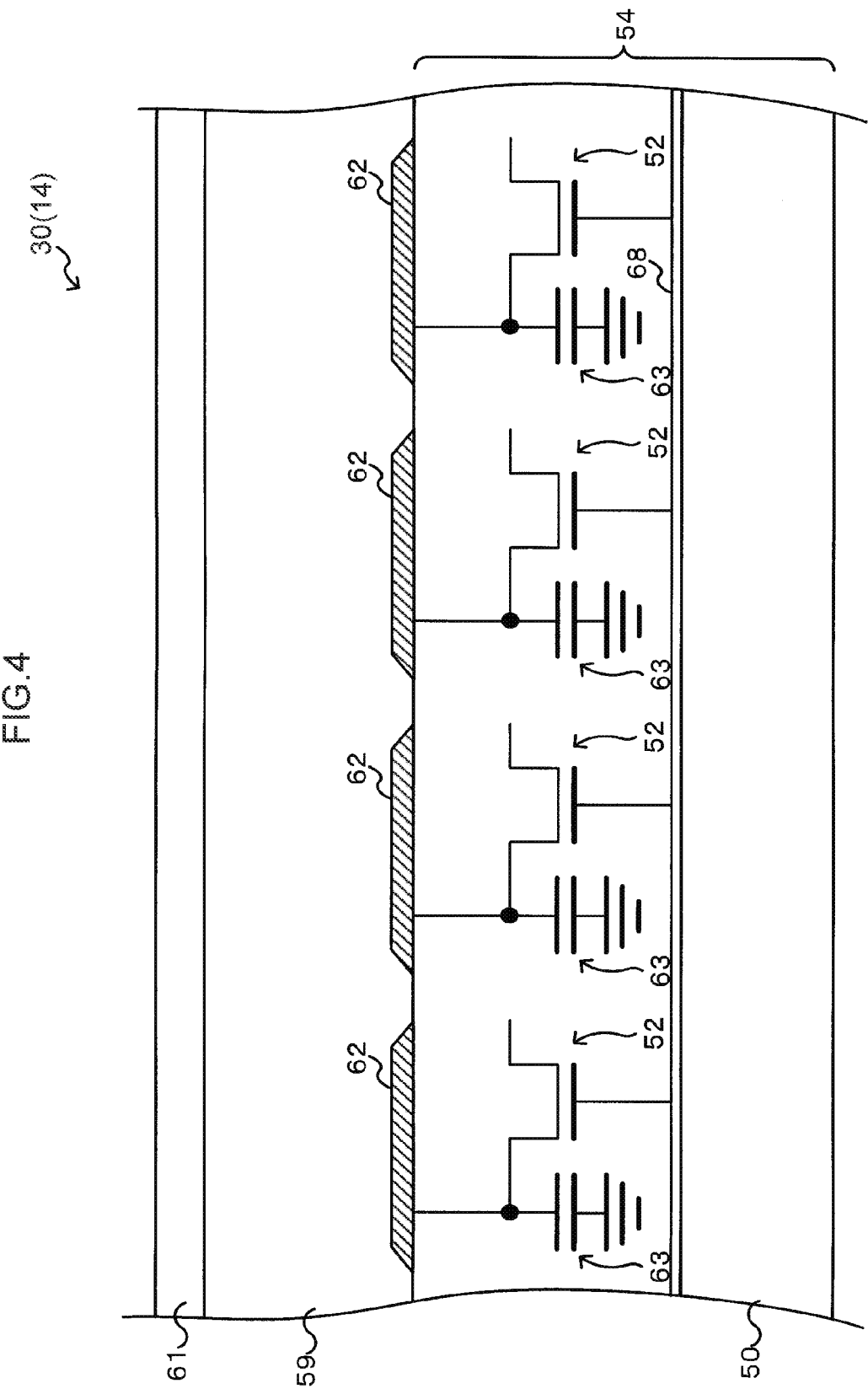
FIG. 4 is a cross-sectional view schematically showing another example of the configuration of the TFT unit of the radiation detector pertaining to the first exemplary embodiment.

The structure and so forth of the TFT unit 30 is not limited to this. The TFT unit 30 may also take another structure as long as it has the function of storing and outputting charges corresponding to the radiation that has been applied to the radiation detector 14. FIG. 4 shows an example of another structure of the TFT unit 30. FIG. 4 is a cross-sectional view schematically showing another example of the configuration of the TFT unit 30. The TFT unit 30 shown in FIG. 4 employs a direct conversion structure that directly converts radiation into charges with a sensor unit using amorphous selenium or the like and stores the charges.

In the TFT unit 30 shown in FIG. 4, as an example of a radiation conversion layer that converts the radiation made incident thereon, a photoconductive layer 59 that converts the radiation made incident thereon into charges is formed on the TFT substrate 54. As the photoconductive layer 59, a compound having, as main component, at least one of: amorphous selenium (a-Se), $Bi_{12}MO_{20}$ (M:Ti, Si, Ge), $Bi_4M_3O_{12}$ (M:Ti, Si, Ge), $Bi_2O_3$, $BiMO_4$ (M:Nb, Ta, V), $Bi_2WO_6$, $Bi_{24}B_2O_{39}$, ZnO, ZnS, ZnSe, ZnTe, $MNbO_3$ (M:Li, Na, K), PbO, $HgI_2$, $PbI_2$, CdS, CdSe, CdTe, $BiI_3$, GaAs, etc., can be used. Among them, an amorphous material is preferred which has high dark resistance, exhibits excellent photoconductivity with respect to radiation application, and is capable of being formed in a layer in a large area at a low temperature by vacuum deposition.

A bias electrode 61 is formed on the front surface of the photoconductive layer 59, which is for applying a bias voltage to the photoconductive layer 59.

In the direct conversion TFT unit 30, as in the indirect conversion TFT unit 30 (see FIG. 3), the charge collecting electrodes 62 that collect the charges generated by the photoconductive layer 59 are formed on the TFT substrate 54.

The TFT substrate 54 in the direct conversion TFT unit 30 is equipped with charge storage capacitors 63 that store the charges collected by the charge collecting electrodes 62. The charges stored in the charge storage capacitors 63 are read out by the switch elements 52. Below, there will be cases where information relating to the charges (charge information) that have been read out from the TFT unit 30 as radiographic image data is called a QL value.

The charges that have been read out in the TFT unit 30 are outputted to the charge amplifier/MUX 32 as electrical signals. The charge amplifier 32 amplifies the electrical signals and converts the amplified electrical signals into analog voltages in the form of electrical information (data). As a specific example, the charge amplifier 32 is configured by an amplification circuit and a sample-and-hold circuit using operational amplifiers and capacitors. The electrical signals held in the sample-and-hold circuit undergo parallel-to-serial conversion in the MUX 32 and are outputted to the A/D converter 34.

The A/D converter 34 converts the serially inputted analog voltages into digital signals that are easier to handle. The two-dimensional image data of the radiographic image converted into the digital signals by the A/D converter 34 are outputted to the control unit 36. In the present exemplary embodiment, an image memory (not shown in the drawings) is connected to the A/D converter 34, and the transmitted image data are stored in sequence in the image memory. In the present exemplary embodiment, the image memory has a storage capacity capable of storing a predetermined number of frames' worth of image data, and each time the capture of a radiographic image is performed, the image data obtained by the imaging are sequentially stored in the image memory.

The control unit 36 is configured by a microcomputer, includes a CPU 36A, a memory 36B including a ROM and a RAM, and a nonvolatile storage unit 36C formed of a flash memory or the like. The control unit 36 controls the actions of the entire radiation detector 14 by executing, with the CPU 36A, various programs stored in the memory 36B.

The control unit 36 performs control to read the QL value when an imaging menu is registered, determine whether or not the read QL value is equal to or greater than a threshold value stored in the storage unit 36C, and, in a case in which the QL value is equal to or greater than the threshold value, determine that radiation has been applied from the radiation applicator 16, start capturing a radiographic image of the subject 19, and acquire image data. Further, when an imaging menu is registered, the control unit 36 of the present exemplary embodiment instructs the threshold value changing unit 44 to acquire a threshold value corresponding to temperature data of the TFT unit 30 and change the threshold value (details of these processes will be described later).

Under the control of the control unit 36, the threshold value changing unit 44 acquires data relating to the temperature (temperature data) of the TFT unit 30, acquires a threshold value corresponding to the temperature data, and changes the threshold value stored in the storage unit 36C of the control unit 36 to the acquired threshold value. That is, the threshold value changing unit 44 changes the threshold value stored in the storage unit 36C in accordance with the temperature data of the TFT unit 30.

The temperature detecting unit 46 detects the temperature of the TFT unit 30. Specific examples of the temperature detecting unit 46 include a thermistor. The temperature detecting unit 46 is not limited to one that directly detects the temperature of the TFT unit 30 and may also be one that detects the temperature inside the radiation detector 14; however, it is preferable that the temperature detecting unit 46 be disposed in a place close to the TFT unit 30.

The image data are further transmitted from the control unit 36 to the wireless communication unit 40. The wireless communication unit 40 wirelessly transmits in packets the image data per line. In this way, the wireless communication unit 40 of the present exemplary embodiment performs wireless communication with an external device (here, the controller 12), is adapted to a wireless LAN standard represented by IEEE (Institute of Electrical and Electronics Engineers) 802.11 a/b/g/n or the like, and controls the transmission of various types of data between the radiation detector 14 and the external device by wireless communication.

Through the wireless communication unit 40, the control unit 36 can perform wireless communication with an external device that controls general operation of radiographic image capturing, such as the controller 12, and can transmit various types of data to and receive various types of data from the controller 12. When capturing a radiographic image of the subject 19, the control unit 36 registers in the storage unit 42 various types of data such as information of the subject 19 and imaging conditions (imaging menu) received via the wireless communication unit 40 from the controller 12 and performs read-out of the charges on the basis of the registered imaging menu.

In this way, the capture of a radiographic image corresponding to the applied radiation is performed in the radiation detector 14. As described above, the capturing action of a radiographic image by the radiation detector 14 is executed without receiving an instruction to capture a radiographic image from the controller 12 and without being synchronized with the application of the radiation by the radiation applicator 16.

Further, the radiation detector 14 is equipped with the power source unit 48. Each of the components described above operates on electrical power supplied from the power source unit 48. The power source unit 48 has a built-in battery (a rechargeable secondary battery) so as to not impair the portability of the radiation detector 14, and the power source unit 48 supplies the electrical power to the components from the charged battery. In FIG. 2, illustration of wires connecting the components to the power source unit 48 is omitted in order to prevent the drawing from becoming complicated.

Figure 5:
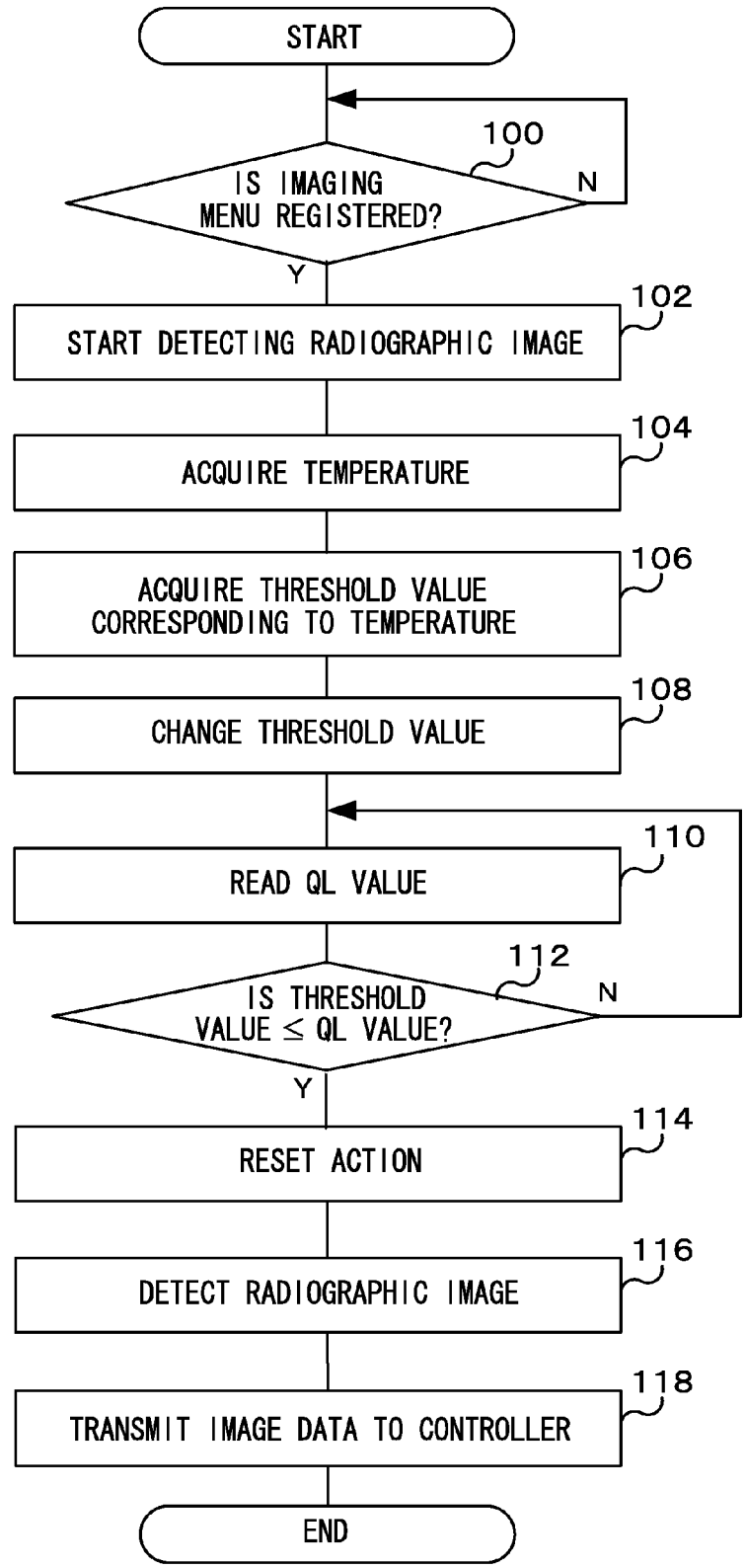
FIG. 5 is a flowchart showing an example of a flow of imaging processing that is executed in the radiation detector pertaining to the first exemplary embodiment.

Next, the radiographic image capturing processing in the radiation detector 14 will be described in detail with reference to the drawings. FIG. 5 is a flowchart showing an example of a flow of radiographic image capturing processing that is executed in the radiation detector 14. When performing the imaging processing, a program stored beforehand in a predetermined area of the memory 36B is executed by the CPU 36A in the control unit 36.

In step 100, the control unit 36 determines whether or not an imaging menu has been registered. If the radiation detector 14 has not yet received an imaging menu from the controller 12, the determination in step 100 is NO and the control unit 36 stands by. If an imaging menu has been registered, the determination in step 100 is YES and the processing advances to step 102. In step 102, the control unit 36 instructs the TFT unit 30 to start detecting the radiographic image (charge information), that is, to start storing the charges.

In step 104, the control unit 36 instructs the threshold value changing unit 44 to acquire the temperature (temperature data) from the temperature detecting unit 46, and in the next step 106, the control unit 36 instructs the threshold value changing unit 44 to acquire the threshold value corresponding to the acquired temperature. According to these instructions, the threshold value changing unit 44 acquires the detected temperature from the temperature detecting unit 46 and acquires the threshold value corresponding to the detected temperature it has acquired. The threshold value corresponding to the detected temperature can be acquired by calculation. Specifically, if the threshold value when the detected temperature is 20° C. is 5500 QL and it is known beforehand that the threshold % value changes 15 QL when the temperature changes 1° C. and 20° C. is taken as an initial value, the QL value that is the threshold value can be obtained by the following expression.

threshold value (QL value)=(detected temperature−20° C.)×15 QL+5500 QL

For example, if the detected temperature is 30° C., (30° C.−20° C.)×15 QL+5500 QL=5650 QL, and the threshold value is 5650 QL.

The method of acquiring the threshold value corresponding to the detected temperature is not limited to this. For example, correspondence between detected temperatures and threshold values may be stored beforehand in the storage unit 42, and the threshold value changing unit 44 may acquire the threshold value on the basis of the correspondence from the storage unit 42.

After the threshold value changing unit 44 acquires the threshold value corresponding to the detected temperature in this way, in the next step 108, the threshold value changing unit 44 changes the threshold value stored in the storage unit 36C of the control unit 36 to the acquired threshold value corresponding to the detected temperature.

After the threshold value corresponding to the detected temperature is set, the control unit 36 performs processing in which it judges the timing when the radiation for capturing a radiographic image of the subject 19 has been applied on the basis of the threshold value.

In the next step 110, the control unit 36 reads the QL value. In the next step 112, the control unit 36 determines whether or not the read QL value is equal to or greater than the threshold value. The method of reading the QL value is not particularly limited. For example, the QL value may be a QL value of pixels determined beforehand, or a QL value of each of pixels that have been read out in plural row units, or a QL value of pixels dedicated to determining the timing of the application of the radiation.

If the read QL value is still less than the threshold value, the determination in step 112 is NO and the processing returns to step 110. If the QL value is equal to or greater than the threshold value, the determination in step 112 is YES, the control unit 36 determines that application of the radiation has been started, and the processing advances to step 114 in order to start capturing a radiographic image of the subject 19.

In step 114, a reset action is performed in which it discharges the charges stored in the TFT unit 30. Thereafter, the processing advances to step 116 in which a radiographic image is detected in the way described above in order to perform radiographic image capture. Thereby, image data of the radiographic image of the subject 19 are acquired.

In the next step 118, the control unit 36 transmits the acquired image data to the controller 12 via the wireless communication unit 40. Thereafter, the control unit 36 ends the present processing.

As described above, the radiation detector 14 of the radiographic image capturing system 10 pertaining to the present exemplary embodiment determines the timing of the application of the radiation for capturing a radiographic image of the subject 19 without synchronizing with the radiation application action of the radiation applicator 16. Further, when an imaging menu is registered from the controller 12, the threshold value changing unit 44 acquires from the temperature detecting unit 46 the temperature of the TFT unit 30, acquires the threshold value corresponding to the detected temperature, and changes the threshold value stored in the storage unit 36C of the control unit 36 to the threshold value corresponding to the detected temperature.

Because of this, the control unit 36 can determine the timing of the application of the radiation on the basis of the threshold value corresponding to the detected temperature and can appropriately determines the application timing regardless of changes in the threshold value resulting from temperature. Consequently, the precision with which the radiation is detected can be improved.

Second Exemplary Embodiment

In the second exemplary embodiment, a case will be described in which a threshold value for determining that radiation has been applied from a radiation applicator in order to capture a radiographic image of a subject is changed in accordance with offset data of a radiographic image (the offset data corresponding to the temperature data in the second exemplary embodiment).

In the radiation detector 14, offset data (offset value) also change in response to temperature because of, for example, changes in characteristics resulting from changes in the temperature of the TFT unit 30. The offset data (offset value) are data of the QL value obtained by reading the QL value with the TFT unit 30 being placed in a state in which the radiation is not being applied.

The radiographic image capturing system 10 and the radiation detector 14 of the present exemplary embodiment have substantially the same configurations as those of the first exemplary embodiment, so detailed description of portions whose configurations are substantially the same will be omitted. The radiation detector 14 of the present exemplary embodiment is not equipped with the temperature detecting unit 46 with which the radiation detector 14 of the first exemplary embodiment (see FIG. 2) is equipped, the control unit 36 acquires offset data for a predetermined period and stores the offset data in the storage unit 42, and the threshold value changing unit 44 acquires a threshold value corresponding to the offset data on the basis of the offset data stored in the storage unit 42 and changes the threshold value stored in the storage unit 36C of the control unit 36.

Figure 6:
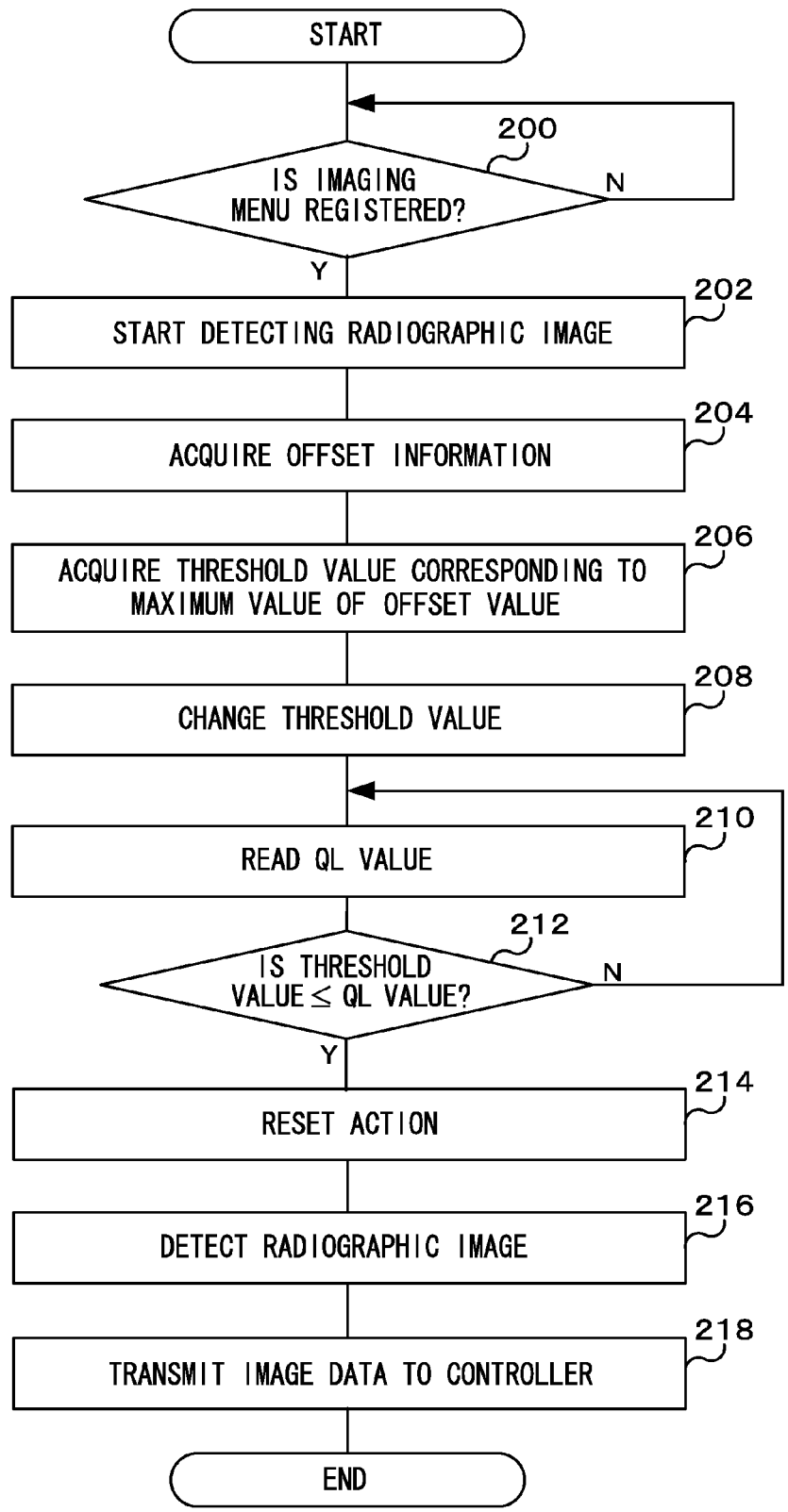
FIG. 6 is a flowchart showing an example of a flow of imaging processing that is executed in a radiation detector pertaining to a second exemplary embodiment.

Next, the radiographic image capturing processing in the radiation detector 14 of the present exemplary embodiment will be described in detail with reference to the drawings. FIG. 6 is a flowchart showing an example of a flow of radiographic image capturing processing that is executed in the radiation detector 14. This imaging processing is substantially the same as the imaging processing executed in the radiation detector 14 of the first exemplary embodiment (see FIG. 5), and therefore, portions corresponding to the imaging processing of the first exemplary embodiment will be indicated as such and detailed description of those will be omitted.

Step 200 of the imaging processing shown in FIG. 6 corresponds to step 100 of the imaging processing of the first exemplary embodiment shown in FIG. 5, and step 202 corresponds to step 102.

Figure 7B:
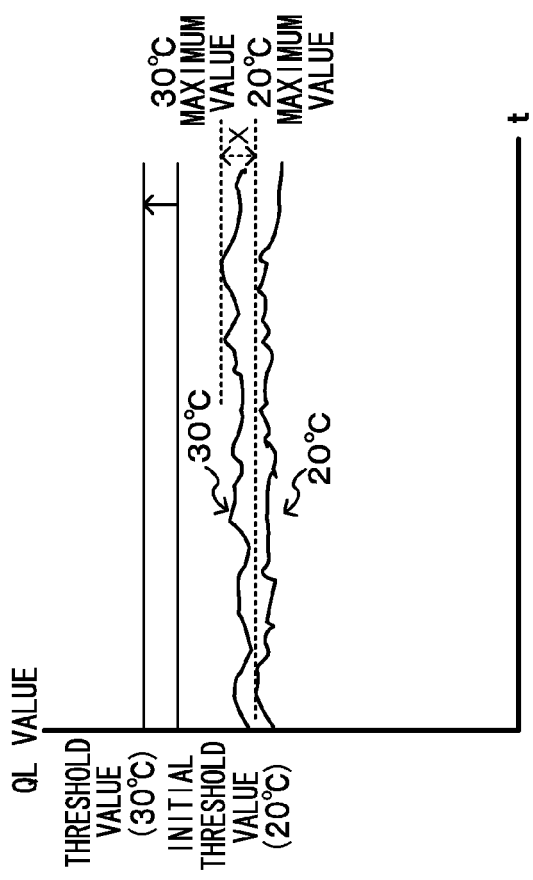
FIG. 7A and FIG. 7B are explanatory diagrams for describing an example of offset data that are acquired in the radiation detector pertaining to the second exemplary embodiment, with FIG. 7A showing an example of the acquired offset data and FIG. 7B showing a change resulting from temperature in a maximum value of an offset value of the acquired offset data and a corresponding change in a threshold value.
Figure 7A:
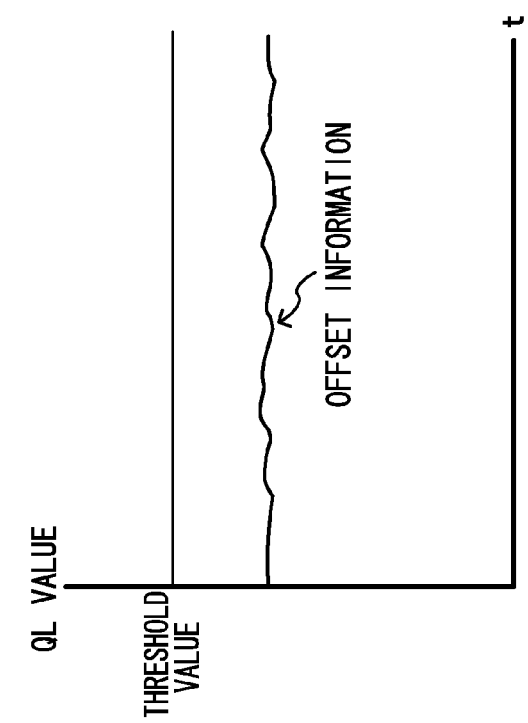

In the next step 204, the control unit 36 acquires the offset data (QL values) for the predetermined period. FIG. 7A shows an example of the acquired offset data. Since radiation is not actually being applied to the TFT unit 30 when the control unit 36 acquires the offset data, the offset value does not exceed the threshold value stored in the storage unit 36C. The predetermined period in which the control unit 36 acquires the offset data can be determined beforehand in consideration of variations in the offset data. In the present exemplary embodiment, the offset data acquired in step 204 are stored in the storage unit 42.

In the next step 206, the threshold value changing unit 44 reads the maximum value of the offset value from the offset data stored in the storage unit 42 and acquires a threshold value corresponding to the maximum value of the read offset value. The threshold value corresponding to the maximum value of the offset value can be acquired by the following method. As shown in FIG. 7B, since the offset data changes, the maximum value of the offset value also changes in response to temperature. Therefore, the threshold value changing unit 44 obtains beforehand the maximum value of the offset value at a predetermined temperature (in FIG. 7B, 20° C. as in the first exemplary embodiment), finds the difference (see X in FIG. 7B) between that maximum value and the maximum value of the offset data it has read from the storage unit 42, and acquires the threshold value corresponding to the difference between the maximum values.

The method of acquiring the threshold value corresponding to the maximum value of the offset value is not limited to this. For example, correspondence between threshold values and maximum values of offset values may be stored beforehand in the storage unit 42, and the threshold value changing unit 44 may acquire the threshold value on the basis of the correspondence from the storage unit 42.

After the threshold value changing unit 44 acquires the threshold value corresponding to the maximum value of the offset value in this way, in the next step 208, the threshold value changing unit 44 changes the threshold value stored in the storage unit 36C of the control unit 36 to the threshold value corresponding to the maximum value of the offset value.

The steps subsequent to step 208 correspond to the imaging processing of the first exemplary embodiment (steps subsequent to step 108 of FIG. 5). Specifically, step 210 corresponds to step 110, step 212 corresponds to step 112, step 214 corresponds to step 114, step 216 corresponds to step 116, and step 218 corresponds to step 118.

In this way, the control unit 36 determines the timing of the application of the radiation by the threshold value corresponding to the maximum value of the offset value (QL value), captures the radiographic image of the subject 19, transmits the image data of the radiographic image to the controller 12, and thereafter ends the present processing.

In the above description, a case in which the threshold value is changed in accordance with the maximum value of the offset value (QL value) has been described, but embodiments are not limited to this. The threshold value can be any threshold value based on the offset data. For example, the threshold value may be a variation in the offset value (QL value) in the predetermined period or a mean value of the offset value (QL value) in the predetermined period.

As described above, the radiation detector 14 of the radiographic image capturing system 10 pertaining to the present exemplary embodiment determines the timing of the application of the radiation for capturing a radiographic image of the subject 19 without synchronizing with the radiation application action of the radiation applicator 16. Further, the control unit 36 acquires the offset data beforehand and stores the offset data in the storage unit 42, and when an imaging menu is registered from the controller 12, the threshold value changing unit 44 reads the maximum value of the offset value (QL value) from the storage unit 42, acquires the threshold value corresponding to the maximum value of the read offset value (QL value), and changes the threshold value stored in the storage unit 36C of the control unit 36 to the threshold value corresponding to the maximum value of the offset value.

Because the control unit 36 can determine the timing of the application of the radiation on the basis of the threshold value corresponding to the offset data, the control unit 36 can appropriately determine the application timing regardless of changes in the QL value resulting from temperature. Consequently, the precision with which the radiation is detected can be improved.

As described above regarding the first and second exemplary embodiments, the threshold value changing unit 44 of the radiation detector 14 changes the threshold value stored in the storage unit 36C of the control unit 36 in accordance with the temperature data of the TFT unit 30. Since the control unit 36 determines, on the basis of the threshold value corresponding to the temperature data of the TFT unit 30, that the radiation for capturing a radiographic image of the subject 19 has been applied, the precision with which the radiation is detected can be improved.

The changing method of the threshold value stored in the storage unit 36C of the control unit 36 is not limited to only those employed the first and second exemplary embodiments. The threshold value stored in the storage unit 36C of the control unit 36 may also be changed in accordance with other factors, such as the type, material, size, area, and thickness of the radiation detector 14.

In addition, the configurations of the radiographic image capturing system 10, the controller 12, the radiation detector 14, the radiation applicator 16, and so forth described in the exemplary embodiments are examples and can be changed depending on the situation without departing from the gist of the present invention.

Further, the flows of the imaging processing described in exemplary embodiments (FIG. 5 and FIG. 6) are also examples and can be changed depending on the situation without departing from the gist of the present invention.

Further, in the exemplary embodiments, cases in which X-rays are applied as the radiation have been described, but embodiments are not limited to this, and other type of radiation such as gamma rays or the like can be also used.

What is claimed is:

1. A radiation detector comprising:
    an image data detecting unit that detects, as radiographic image data, charge information corresponding to applied radiation, wherein the image data detecting unit detects offset data after the radiation detector having received imaging conditions from an external controller, the offset data is obtained by performing for a predetermined period detection by the image data detecting unit without applying radiation;
    a changing unit that changes a threshold value in accordance with temperature data of the image data detecting unit, wherein a maximum value of the offset data is used as the temperature data; and
    a control unit that determines, while keeping the threshold value unchanged, that radiation has been applied if a read value of the detected charge information is equal to or greater than the threshold value and, if it is determined that application of radiation has been started, controls the image data detecting unit to acquire radiographic image data corresponding to radiation that has passed through a subject.

2. A radiographic image capturing system comprising:
    a controller that instructs a setting relating to capturing radiographic data;
    a radiation applicator that applies radiation on the basis of an instruction from the controller; and
    the radiation detector according to claim 1, which detects radiographic image data corresponding to the radiation that has been applied from the radiation applicator.

3. A non-transitory storage medium storing a program causing a computer to execute radiation detection processing, the radiation detection processing comprising:
    configuring an image data detecting unit to detect charge information corresponding to applied radiation;
    detecting, by the image data detecting unit, offset data after having received imaging conditions, the offset data is obtained by performing for a predetermined period detection by the image data detecting unit without applying radiation;
    changing a threshold value in accordance with temperature data of the image data detecting unit, wherein a maximum value of the offset data is used as the temperature data;
    detecting, by the image data detecting unit, charge information corresponding to applied radiation; and
    determining, while keeping the threshold value unchanged, that radiation has been applied if a read value of the detected charge information is equal to or greater than the threshold value and, if it is determined that application of radiation has been started, controlling the image data detecting unit to detect radiographic image data corresponding to radiation that has passed through a subject.

* * * * *